United States Patent [19]

Kumar et al.

[11] Patent Number: 5,651,923

[45] Date of Patent: Jul. 29, 1997

[54] SUBSTITUTED NAPHTHOPYRANS

[75] Inventors: Anil Kumar; David B. Knowles; Barry Van Gemert, all of Pittsburgh, Pa.

[73] Assignee: Transitions Optical, Inc., Pinellas Park, Fla.

[21] Appl. No.: 571,000

[22] Filed: Dec. 12, 1995

Related U.S. Application Data

[63] Continuation-in-part of Ser. No. 490,189, Jun. 14, 1995, abandoned, which is a continuation-in-part of Ser. No. 164,187, Dec. 9, 1993, Pat. No. 5,458,814.

[51] Int. Cl.$^6$ .................. C08K 5/15; C07D 311/78; C07D 405/02; G02B 5/23

[52] U.S. Cl. .................. 252/586; 549/382; 549/381; 549/362; 549/331; 549/214; 548/525; 548/518; 548/455; 548/454; 548/440; 548/418; 548/417; 548/407; 548/406; 548/311.7; 548/364.4; 546/214; 546/213; 546/208; 546/207; 546/201; 546/196; 546/165; 546/276.7; 546/281.1; 546/282.7; 544/375; 544/373; 544/372; 544/370; 544/360; 544/150; 544/145; 544/142; 524/110; 524/109; 524/90; 524/84

[58] Field of Search .................. 549/382, 381, 549/362, 331, 214; 548/418, 417, 407, 406, 374, 336, 525, 440, 455, 454, 518; 546/214, 213, 208, 207, 273, 269, 196, 201, 165; 544/375, 373, 150, 145, 142, 360, 370, 372; 524/110, 109, 90, 84; 252/586

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Casella et al. | 252/300 |
| 4,215,010 | 7/1980 | Hovey et al. | 252/300 |
| 4,342,668 | 8/1982 | Hovey et al. | 252/586 |
| 4,637,698 | 1/1987 | Kwak et al. | 351/163 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,880,667 | 11/1989 | Welch | 427/160 |
| 4,931,219 | 6/1990 | Kwiatkowski et al. | 252/160 |
| 4,980,089 | 12/1990 | Heller | 252/586 |
| 4,994,208 | 2/1991 | McBain et al. | 252/586 |
| 5,066,818 | 11/1991 | Van Gemert | 549/389 |
| 5,200,116 | 4/1993 | Heller | 252/586 |
| 5,238,981 | 8/1993 | Knowles | 524/110 |
| 5,244,602 | 9/1993 | Van Gemert | 252/589 |
| 5,274,132 | 12/1993 | Van Gemert | 549/389 |
| 5,384,077 | 1/1995 | Knowles | 252/586 |
| 5,405,958 | 4/1995 | Van Gemert | 544/71 |
| 5,411,679 | 5/1995 | Kumar | 252/586 |
| 5,451,344 | 9/1995 | Knowles et al. | 252/586 |
| 5,458,814 | 10/1995 | Kumar et al. | 252/586 |
| 5,464,567 | 11/1995 | Knowles et al. | 252/586 |
| 5,466,398 | 11/1995 | Van Gemert et al. | 252/586 |

FOREIGN PATENT DOCUMENTS

| | | |
|---|---|---|
| 62-195383 | 8/1987 | Japan . |
| 7-41758 | 2/1995 | Japan . |
| 7-48363 | 2/1995 | Japan . |
| 7-48566 | 2/1995 | Japan . |
| 7-48567 | 2/1995 | Japan . |

OTHER PUBLICATIONS

*Friedel–Crafts and Related Reactions*, George A. Olah, Interscience Publishers, vol. 3 Chapter XXXI, pp. 1–8, 1964.

"Regioselective Friedel Crafts Acylation of 1,2,3,4–Tetrahydroquinoline and Related Nitrogen Heterocycles: Effects of NH Protective Groups and Ring Size", Ishihara, Y., et al., J. Chem. Soc., Perkin Trans. 1, pp. 3401–3406, 1992.

"Fast Fading Naphtho[1,2–b]pyran Photochromics", Research Disclosure, May 1994, pp. 267–268.

*Heterocyclic Compounds*, Elderfield, R.C., 1951, vol. 2, Chapters 3 and 5, pp. 123–144, 164–172.

*The Chemistry of Heterocyclic Compounds*, Hartough, H.D. and Meisel, S.L., 1954, vol. 7, Chapter IV, "Dibenzothiophene and Its Derivatives", pp. 225–282.

*Advances in Heterocyclic Chemistry*, Katritzky, A.R. and Boulton, A.J., 1974, vol. 16, Chapter V, "Recent Advances in the Chemistry of Dibenzothiophenes", pp. 181–288.

*Heterocyclic Compounds*, Elderfield, R.C., 1952, vol. 3, Chapter 3, "The Chemistry of Carbazole" pp. 291–341.

*Organic Reactions*, vol. VI, John Wiley & Sons, Inc., Chapter 1, pp. 1–2 (1951).

*Organic Synthesis*, vol. 31, John wiley and Sons, Inc. pp. 90–92 (1951).

*Organic Synthesis*, vol. 32, John Wiley and Sons, Inc. pp. 72–76 (1952).

S. P. Adams et al., "Synthesis, Conformation, and Complexation Behavior of 2,9–18–25–Tetraoxa[8,8](1,4)naphthalenophane", J. Org. Chem. 1981, 46, pp. 3474–3478.

*Primary Examiner*—Nicky Chan
*Attorney, Agent, or Firm*—Frank P. Mallak; Irwin M. Stein

[57] ABSTRACT

Described are novel reversible photochromic 2H-naphtho[1,2-b]pyran compounds, examples of which are compounds fused on the naphtho-portion of the naphthopyran ring with an indeno group or certain heterocyclic substituents. Certain substituents are also present at the 2 and 5 positions and sometimes at the 6 position of the naphthopyran ring. Also described are organic host materials that contain or that are coated with such compounds. Articles such as ophthalmic lenses or other plastic transparencies that incorporate the novel naphthopyran compounds or combinations thereof with complementary photochromic compounds, e.g., spiro (indoline) type compounds, are also described.

21 Claims, No Drawings

SUBSTITUTED NAPHTHOPYRANS

CROSS REFERENCE TO RELATED APPLICATIONS

This application is a continuation in part of application Ser. No. 08/490,189 filed Jun. 14, 1995, now abandoned, which was a continuation in part of application Ser. No. 08/164,187, filed Dec. 9, 1993 which issued as U.S. Pat. No. 5,458,814.

DESCRIPTION OF THE INVENTION

The present invention relates to certain novel naphthopyran compounds. More particularly, this invention relates to novel photochromic naphthopyran compounds and to compositions and articles containing such novel naphthopyran compounds. When exposed to light radiation involving ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in the '818 patent are the isomeric 2,2-diaryl-2H-naphtho[1,2-b]pyrans, which are reported to require unacceptably long periods of time to fade after activation.

U.S. Pat. No. 3,627,690 describes photochromic 2,2-di-substituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho-[1,2-b]pyrans without the aforementioned additives ranges from several hours to many days to reach complete reversion. U.S. Pat. No. 4,818,096 discloses a blue coloring photochromic benzo- or naphthopyran having at the position alpha to the oxygen of the pyran ring a phenyl group having a nitrogen containing substituent in the ortho or para positions.

The present invention relates to novel substituted 2H-naphtho[1,2-b]pyran compounds which have been unexpectedly found to have an acceptable fade rate in addition to a high activated intensity and a high coloration rate. In particular, the use of certain substituents at the 5-position of the naphtho-portion of the naphthopyran compound increases the fade rate without the addition of acids or bases. In addition, these compounds have certain substituents at the 2-position of the pyran ring, as well as an indeno group fused to the i, j or k face of the naphthopyran or certain heterocyclic rings fused to the f, i, j or k face of the naphthopyran.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

In accordance with the present invention, it has now been discovered that certain novel 2H-naphtho[1,2-b]pyran compounds having an acceptable fade rate, high activated intensity and a high coloration rate may be prepared. These compounds may be described as naphthopyrans having an indeno group annelated on the i, j or k side of the naphthopyran ring or certain heterocyclic substituents annelated on the f, i, j or k side of the naphthopyran ring. Certain substituents are also present at the 2 and 5 positions and sometimes at the 6 position of the naphthopyran ring. These compounds may be represented by the following graphic formulae I, which includes the side letters, or I A, which includes the atom numbers:

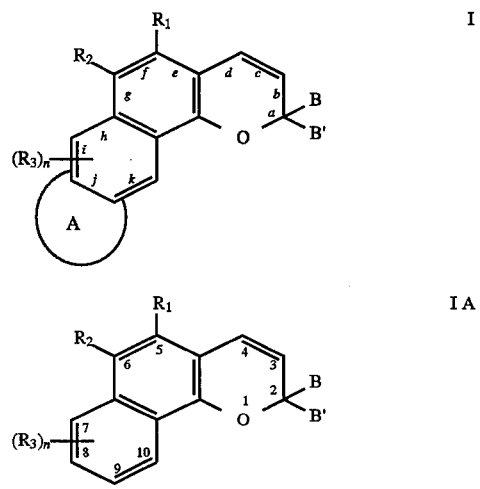

In graphic formula I, A may be selected from the group consisting of (i) an unsubstituted, mono-substituted or di-substituted heterocyclic ring selected from the group consisting of benzothieno, benzofurano and indolo, the 2,3 or 3,2 positions of the heterocyclic ring being fused to the i, j or k side of the naphthopyran; and (ii) an unsubstituted, mono-substituted or di-substituted indeno group fused to the i, j or k side of the naphthopyran. The indeno group and heterocyclic ring substituents are each $C_1$–$C_6$ alkyl, $C_5$–$C_7$ cycloalkyl, $C_1$–$C_6$ alkoxy, chloro, fluoro, an unsubstituted or mono-substituted benzo group fused to the benzo portion of the benzothieno, benzofurano, indeno or indolo moieties, said benzo substitutents being $C_1$–$C_6$ alkyl, $C_5$–$C_7$ cycloalkyl, $C_1$–$C_6$ alkyl mono-substituted ($C_5$–$C_7$) cycloalkyl, $C_1$–$C_6$ alkoxy, chloro or fluoro. Preferably, A is selected from the group consisting of (i) an unsubstituted or mono-substituted heterocyclic ring, the heterocyclic ring substituents being $C_1$–$C_4$ alkyl, $C_1$–$C_3$ alkoxy or benzo; and (ii) an unsubstituted or mono-substituted indeno group. More preferably, A is selected from the group consisting of (i) an unsubstituted or mono-substituted heterocyclic ring, the 2,3 or 3,2 position of said heterocyclic ring being fused to the i or k side of the naphthopyran, and the heterocyclic ring substituents being $C_1$–$C_3$ alkyl, $C_1$–$C_3$ alkoxy or benzo;

and (ii) an unsubstituted or mono-substituted indeno group fused to the i or k side of said naphthopyran. Most preferably, A is selected from the group consisting of (i) an unsubstituted or mono-substituted benzothieno or benzofurano group, said group substituents being $C_1$–$C_2$ alkyl, $C_1$–$C_2$ alkoxy or benzo; and (ii) an indeno group.

$R_1$ in graphic formulae I and I A may be selected from the group consisting of: (i) —C(O)W, W being —$OR_4$ or —N($R_5$)$R_6$, wherein $R_4$ is hydrogen, allyl, $C_1$–$C_6$ alkyl, unsubstituted or mono-substituted phenyl, unsubstituted or mono-substituted phenyl($C_1$–$C_3$)alkyl, mono($C_1$–$C_6$)alkoxy ($C_2$–$C_4$)alkyl, or $C_1$–$C_6$ haloalkyl; $R_5$ and $R_6$ are each selected from the group consisting of hydrogen, $C_1$–$C_6$ alkyl, $C_5$–$C_7$ cycloalkyl, unsubstituted, mono-substituted and di-substituted phenyl, or $R_5$ and $R_6$ together with the nitrogen atom form an unsubstituted, mono-substituted or di-substituted heterocyclic ring selected from the group consisting of 1-indolinyl, morpholino, piperidino, 1-pyrrolidyl, 1-imidazolidyl, 2-imidazolin-1-yl, pyrazolidyl, pyrazolinyl and 1-piperazinyl; and (ii) —C($R_{11}$)$_2$X, wherein X is —CN, halogen, hydroxy, benzoyloxy, $C_1$–$C_6$ alkoxy, $C_2$–$C_6$ acyloxy, amino, $C_1$–$C_6$ monoalkylamino, $C_1$–$C_6$ dialkylamino, morpholino, piperidino, 1-indolinyl, pyrrolidyl or trimethylsilyloxy, $R_{11}$ is hydrogen, $C_1$–$C_6$ alkyl, phenyl or naphthyl, each of said described phenyl and heterocyclic ring substituents being $C_1$–$C_6$ alkyl or $C_1$–$C_6$ alkoxy, and each of said described halogen or halo substituents being chloro or fluoro.

Preferably, $R_1$ is selected from the group consisting of: (i) —C(O)W, W being —$OR_4$ or —N($R_5$)$R_6$, wherein $R_4$ is hydrogen, $C_1$–$C_4$ alkyl, unsubstituted or mono-substituted phenyl, unsubstituted or mono-substituted phenyl($C_1$–$C_3$) alkyl, mono($C_1$–$C_4$)alkoxy($C_2$–$C_3$)alkyl, or $C_1$–$C_4$ haloalkyl, and wherein $R_5$ and $R_6$ are each selected from the group consisting of hydrogen, $C_1$–$C_4$ alkyl, $C_5$–$C_7$ cycloalkyl, unsubstituted, mono-substituted and di-substituted phenyl, or $R_5$ and $R_6$ together with the nitrogen atom form an unsubstituted, mono-substituted or di-substituted heterocyclic ring selected from the group consisting of 1-indolinyl, morpholino, piperidino and 1-pyrrolidyl; and (ii) —C($R_{11}$)$_2$X, wherein X is —CN, halogen, hydroxy, benzoyloxy, $C_1$–$C_4$ alkoxy, $C_2$–$C_4$ acyloxy, amino, $C_1$–$C_4$ mono-alkylamino, $C_1$–$C_4$ dialkylamino, morpholino, piperidino, 1-indolinyl or pyrrolidyl, $R_{11}$ is hydrogen, $C_1$–$C_4$ alkyl, phenyl or naphthyl; and each of said described phenyl and heterocyclic ring substituents being $C_1$–$C_4$ alkyl or $C_1$–$C_4$ alkoxy, and each of said described halogen or halo substituents being chloro or fluoro.

More preferably, $R_1$ is selected from the group consisting of: (i) —C(O)W, W being —$OR_4$ or —N($R_5$)$R_6$, wherein $R_4$ is hydrogen, $C_1$–$C_3$ alkyl, unsubstituted or mono-substituted phenyl, mono($C_1$–$C_3$)alkoxy($C_2$–$C_3$)alkyl or $C_1$–$C_3$ fluoroalkyl, and wherein $R_5$ and $R_6$ are each selected from the group consisting of hydrogen, $C_1$–$C_3$ alkyl, $C_5$–$C_7$ cycloalkyl, unsubstituted and mono-substituted phenyl, or $R_5$ and $R_6$ together with the nitrogen atom form an unsubstituted or mono-substituted heterocyclic ring selected from the group consisting of morpholino and piperidino, each of said described phenyl and heterocyclic ring substituents being $C_1$–$C_3$ alkyl or $C_1$–$C_3$ alkoxy; and (ii) —C($R_{11}$)$_2$X, wherein X is fluoro, hydroxy, benzoyloxy, $C_1$–$C_3$ alkoxy, $C_2$–$C_3$ acyloxy, amino, $C_1$–$C_3$ mono-alkylamino, $C_1$–$C_3$ dialkylamino, morpholino or piperidino, and $R_{11}$ is hydrogen, $C_1$–$C_3$ alkyl, phenyl or naphthyl.

Most preferably, $R_1$ is selected from the group consisting of: (i) —C(O)W, W being —$OR_4$ or —N($R_5$)$R_6$, wherein $R_4$ is $C_1$–$C_3$ alkyl, $R_5$ and $R_6$ are each hydrogen, $C_1$–$C_3$ alkyl or phenyl, or $R_5$ and $R_6$ together with the nitrogen atom form morpholino or piperidino; and (ii) —C($R_{11}$)$_2$X, wherein X is fluoro, hydroxy, $C_1$–$C_2$ alkoxy, acetoxy, amino, $C_1$–$C_2$ monoalkylamino, $C_1$–$C_2$ dialkylamino, morpholino or piperidino, and $R_{11}$ is hydrogen or $C_1$–$C_2$ alkyl.

In graphic formulae I and I A, $R_2$ may be hydrogen, $C_1$–$C_6$ alkyl, the mono-, di- or tri-substituted aryl groups phenyl or naphthyl, the aryl substituents being $C_1$–$C_6$ alkyl, $C_1$–$C_6$ alkoxy, chloro or fluoro; or $R_1$ and $R_2$ together form an unsubstituted, mono-substituted or di-substituted heterocyclic ring selected from the group consisting of benzothieno, benzofurano and indolo, provided that the 2,3 or 3,2 positions of said heterocyclic ring are fused to the f side of said naphthopyran, provided further there is only one heterocyclic ring A fused to the naphthopyran, i.e., if A is not fused to the i, j, or k side of the naphtho-portion of the naphthopyran, then $R_1$ and $R_2$ together may form the heterocyclic ring. Preferably, $R_2$ is hydrogen, $C_1$–$C_4$ alkyl, the mono- or di-substituted aryl groups phenyl or naphthyl, the aryl substituents being $C_1$–$C_4$ alkyl, $C_1$–$C_4$ alkoxy, chloro or fluoro; or $R_1$ and $R_2$ come together to form the aforedescribed preferable heterocyclic ring A. More preferably, $R_2$ is hydrogen, $C_1$–$C_3$ alkyl, the mono- or di-substituted aryl groups phenyl or naphthyl, the aryl substituents being $C_1$–$C_3$ alkyl, $C_1$–$C_3$ alkoxy or fluoro; or $R_1$ and $R_2$ come together to form the aforedescribed heterocyclic ring A. Most preferably, $R_2$ is hydrogen, $C_1$–$C_2$ alkyl, mono- or di-substituted phenyl, the phenyl substituents being $C_1$–$C_2$ alkyl, $C_1$–$C_2$ alkoxy or fluoro; or $R_1$ and $R_2$ together form an unsubstituted or mono-substituted benzothieno or benzofurano group.

In graphic formulae I and I A, each $R_3$ may be fluoro, chloro, $C_1$–$C_4$ alkyl, $C_1$–$C_4$ alkoxy, the group, —N($R_5$)$R_6$, as described for $R_1$, phenyl, naphthyl, phenoxy or naphthoxy, and n is selected from the integers 0, 1 or 2, provided that group A is present, or each $R_3$ is fluoro, chloro, the group, —N($R_5$)$R_6$, phenoxy or naphthoxy, and n is selected from the integers 1, 2 or 3, provided that group A is absent. Preferably, each $R_3$ is fluoro, $C_1$–$C_4$ alkyl, $C_1$–$C_4$ alkoxy, the group, —N($R_5$)$R_6$, phenyl, naphthyl, phenoxy or naphthoxy, and n is selected from the integers 0 or 1, provided that group A is present, or each $R_3$ is fluoro, morpholino, phenoxy or naphthoxy, and n is selected from the integers 1 or 2, provided that group A is absent. More preferably, each $R_3$ is fluoro, $C_1$–$C_3$ alkyl, $C_1$–$C_3$ alkoxy, morpholino, phenoxy or naphthoxy, and n is selected from the integers 0 or 1, provided that group A is present, or each $R_3$ is fluoro, morpholino, phenoxy or naphthoxy, and n is selected from the integers 1 or 2, provided that group A is absent. Most preferably, each $R_3$ is fluoro, $C_1$–$C_2$ alkyl, $C_1$–$C_2$ alkoxy, morpholino, phenoxy or naphthoxy, and n is selected from the integers 0 or 1, provided that group A is present, or each $R_3$ is fluoro, morpholino, phenoxy or naphthoxy, and n is selected from the integers 1 or 2, provided that group A is absent.

In graphic formula I and I A, B and B' may each be selected from the group consisting of: (i) the unsubstituted, mono-, di- and tri-substituted aryl groups phenyl and naphthyl; (ii) the unsubstituted, mono- and di-substituted heterocyclic aromatic groups pyridyl, furanyl, benzofuran-2-yl, benzofuran-3-yl, thienyl, benzothien-2-yl, benzothien-3-yl, dibenzothienyl, dibenzofuranyl and carbazolyl, the aryl and heterocyclic group substituents being selected from the group consisting of hydroxy, amino, $C_1$–$C_6$ monoalkylamino, $C_1$–$C_6$ dialkylamino, i.e., di-($C_1$–$C_6$) alkylamino, morpholino, piperidino, 1-indolinyl, pyrrolidyl, 1-imidazolidyl, 2-imidazolin-1-yl, 2-pyrazolidyl, pyrazolinyl, 1-piperazinyl, $C_1$–$C_6$ alkyl, $C_1$–$C_6$ haloalkyl, $C_1$–$C_6$ alkoxy, mono($C_1$–$C_6$)alkoxy($C_1$–$C_4$)alkyl, acryloxy, methacryloxy and halogen, wherein each of the described halogen or (halo) group may be fluoro or chloro; (iii) the groups represented by the following graphic formulae II A and II B:

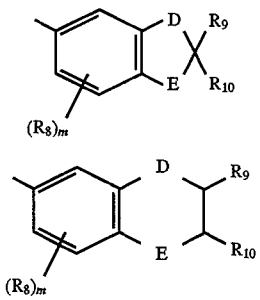

wherein D may be carbon or oxygen and E may be oxygen or substituted nitrogen, provided that when E is substituted nitrogen, D is carbon, said nitrogen substituent being selected from the group consisting of hydrogen, $C_1$–$C_6$ alkyl and $C_2$–$C_6$ acyl; each $R_8$ may be $C_1$–$C_6$ alkyl, $C_1$–$C_6$ alkoxy, hydroxy or halogen, wherein the halogen may be chloro or fluoro; $R_9$ and $R_{10}$ may each be hydrogen or $C_1$–$C_6$ alkyl; and m may be the integer 0, 1 or 2; (iv) $C_1$–$C_6$ alkyl, $C_1$–$C_6$ haloalkyl, $C_1$–$C_6$ alkoxy($C_1$–$C_4$)alkyl, $C_3$–$C_6$ cycloalkyl, mono($C_1$–$C_6$)alkoxy($C_3$–$C_6$)cycloalkyl, mono($C_1$–$C_6$)alkyl ($C_3$–$C_6$)cycloalkyl, and halo($C_3$–$C_6$)cycloalkyl, each of said halo groups being fluoro or chloro; and (v) the group represented by the following graphic formula II C:

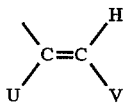

wherein U may be hydrogen or $C_1$–$C_4$ alkyl, and V may be selected from the unsubstituted, mono- and di-substituted members of the group consisting of naphthyl, phenyl, furanyl and thienyl, wherein the substituents for each member of said group are $C_1$–$C_4$ alkyl, $C_1$–$C_4$ alkoxy, fluoro or chloro; or (vi) B and B' taken together form an unsubstituted, mono- or di-substituted fluoren-9-ylidene or form a member selected from the group consisting of saturated $C_3$–$C_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene, cycloundecylidene and cyclododecylidene, saturated $C_7$–$C_{12}$ spiro-bicyclic hydrocarbon rings, e.g., bicyclo[2.2.1]heptylidene, i.e., norbornylidene, 1,7,7-trimethyl bicyclo[2.2.1]heptylidene, i.e., bornylidene, bicyclo[3.2.1]octylidene, bicyclo[3.3.1]nonan-9-ylidene and bicyclo[4.3.2]undecane, and saturated $C_7$–$C_{12}$ spiro-tricyclic hydrocarbon rings, e.g., tricyclo [2.2.1.0$^{2,6}$]heptylidene, tricyclo[5.3.1.1$^{2,6}$]dodecylidene and tricyclo[3.3.1.1$^{3,7}$]decylidene, i.e., adamantylidene, wherein the fluoren-9-ylidene substituents may be selected from the group consisting of $C_1$–$C_4$ alkyl, $C_1$–$C_4$ alkoxy, fluoro and chloro.

Preferably, B and B' are each selected from the group consisting of: (i) unsubstituted, mono-, di- and tri-substituted phenyl; (ii) the unsubstituted, mono- and di-substituted heterocyclic aromatic groups pyridyl, furanyl, benzofuran-2-yl, benzofuran-3-yl, thienyl, benzothien-2-yl, benzothien-3-yl, dibenzothienyl, dibenzofuranyl and carbazolyl, each of the phenyl and heterocyclic substituents being selected from the group consisting of morpholino, piperidino, $C_1$–$C_4$ alkyl, $C_1$–$C_4$ alkoxy and halogen, the halogen being fluoro or chloro; (iii) the groups represented by the graphic formula II A, wherein D is carbon and E is oxygen; each $R_8$ is $C_1$–$C_4$ alkyl, $C_1$–$C_4$ alkoxy, hydroxy or halogen, the halogen being chloro or fluoro; $R_9$ and $R_{10}$ are each hydrogen or $C_1$–$C_4$ alkyl; and m is the integer 0, 1 or 2; (iv) $C_1$–$C_4$ alkyl, $C_1$–$C_6$ alkoxy($C_1$–$C_4$)alkyl and $C_3$–$C_6$ cycloalkyl; and (v) the group represented by graphic formula II C, wherein U is hydrogen or methyl, and V is phenyl or mono-substituted phenyl, the phenyl substituent being $C_1$–$C_4$ alkyl, $C_1$–$C_4$ alkoxy or fluoro; or (vi) B and B' taken together form an unsubstituted or mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings and saturated $C_7$–$C_{10}$ spiro-tricyclic hydrocarbon rings, said fluoren-9-ylidene substituents being selected from $C_1$–$C_3$ alkyl, $C_1$–$C_3$ alkoxy and fluoro.

More preferably, B and B' are each selected from the group consisting of: (i) unsubstituted, mono- and di-substituted phenyl; (ii) the unsubstituted, mono- and di-substituted heterocyclic aromatic groups pyridyl, benzofuran-2-yl, benzothien-2-yl, dibenzothienyl and dibenzofuranyl, each of the phenyl and heterocyclic substituents being selected from the group consisting of morpholino, piperidino, $C_1$–$C_2$ alkyl and $C_1$–$C_2$ alkoxy; and (iii) the groups represented by graphic formula II A, wherein D is carbon and E is oxygen; each $R_8$ is $C_1$–$C_2$ alkyl, $C_1$–$C_2$ alkoxy or fluoro; $R_9$ and $R_{10}$ are each hydrogen or $C_1$–$C_2$ alkyl; and m is the integer 0, 1 or 2; or (iv) B and B' taken together form fluoren-9-ylidene, bornylidene, norbornylidene, bicyclo[3.3.1]nonan-9-ylidene or adamantylidene. Most preferably, B and B' are each phenyl, methoxy substituted phenyl, morpholino substituted phenyl, dibenzofuran-2-yl, 2,3-dihydrobenzofuran-5-yl or adamantylidene.

Compounds represented by graphic formulae I and I A may be prepared by the following described methods. Benzophenones represented by graphic formula V and VA are either purchased or prepared by Friedel-Crafts methods using an appropriately substituted or unsubstituted benzoyl chloride of graphic formula IV and a commercially available substituted or unsubstituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

In Reaction A, the compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (or VA in Reaction B). R and R' represent potential phenyl substituents.

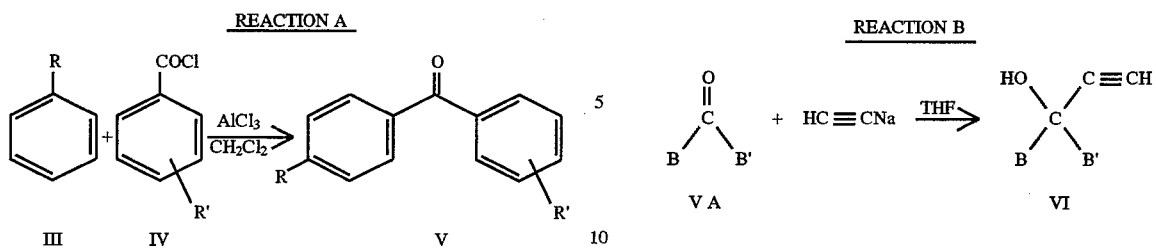

In Reaction B, the substituted or unsubstituted ketone represented by graphic formula V A, in which B and B' may represent groups other than substituted or unsubstituted phenyl, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or for example, from ketones prepared via reaction of an acyl halide with a substituted or unsubstituted benzene, naphthalene, or heteroaromatic compound. Propargyl alcohols having B or B' groups represented by graphic formula II C may be prepared by the methods described in U.S. Pat. No. 5,274,132, column 2, lines 40 to 68.

As shown in Reaction C, the substituted or unsubstituted dihydroxydinaphthofurans, represented by the graphical formula IX, may be prepared by the reaction of a substituted or unsubstituted naphthoquinone, represented by the graphical formula VII, with 1,3-dihydroxynaphthalene, represented by graphical formula VIII. This compound can be methylated to produce a methoxy substituted hydroxy dinaphthofuran, represented by the graphical formula X. Similarly substituted or unsubstituted hydroxy-dinaphthofurans, represented by the graphical formula XII, may be prepared by the reaction of a substituted or unsubstituted naphthoquinone, represented by the graphical formula VII, with 2-hydroxynaphthalene, represented by graphical formula XI. Compounds X and XII are represented more generally by graphic formula XXV B in Reaction G.

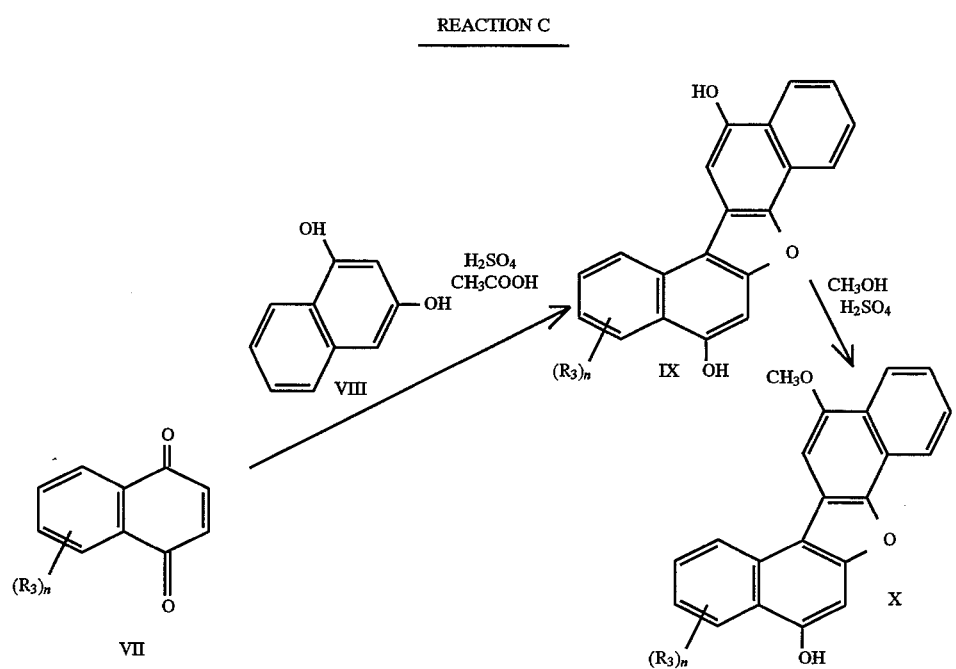

-continued
REACTION C

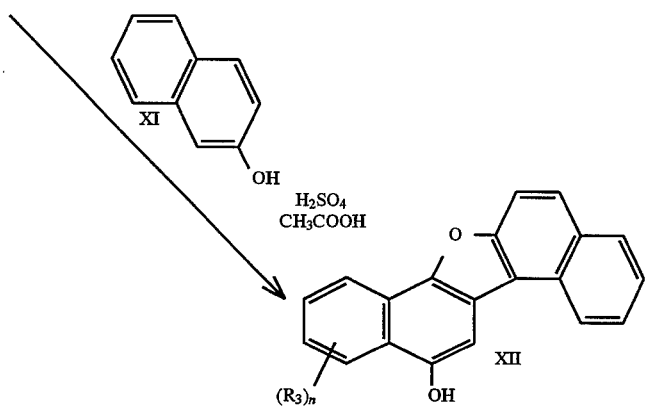

A benzoyl or acetyl derivative of a heterocyclic compound may be prepared by Friedel-Crafts methods. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992; *Heterocyclic Compounds*, Robert C. Elderfield, 1951, Vol. 2, Chapter 3 (Dibenzofuran) and Chapter 5 (Dibenzothiophene); *The Chemistry of Heterocyclic Compounds*, H. D. Hartough and S. L. Meisel, 1954, Vol. 7, Chapter IV (Dibenzothiophene and its Derivatives); *Advances in Heterocyclic Chemistry*, A. R. Katritzky and A. J. Boulton, 1974, Vol. 16, Chapter V (Recent Advances in the Chemistry of Dibenzothiophenes); *Heterocyclic Compounds*, Robert C. Elderfield, 1952, Vol. 3, Chapter 3 (The Chemistry of Carbazole).

In Reaction D, compounds represented by graphic formulae XIII (wherein M is oxygen, nitrogen, sulfur, methylene, mono- or di-substituted methylene and R" represents potential substituents to the A group) and an acyl compound XIV are dissolved in a solvent, such as carbon disulfide or methylene chloride, in the presence of a Lewis acid, such as aluminum chloride, to form the corresponding substituted ketone represented by graphic formula XV.

In Reaction E, the substituted or unsubstituted heterocyclic acyl derivative represented by graphic formula XV is reacted with dimethyl succinate (graphic formula XVI) in the presence of a base such as sodium hydride or a potassium t-butoxide in a suitable solvent such as toluene to form the appropriate substituted monoester of an α-arylidene succinic acid, represented by graphic formula XVII. Other ester substituents, on the compound represented by graphic formula XVII may be prepared by using different succinate esters, such as diethyl succinate. Compound XVII is heated with acetic anhydride and anhydrous sodium acetate to form the corresponding acetate derivative represented by the graphic formula XVIII. Compound XVIII is reacted with hydrochloric acid and an anhydrous alcohol such as anhydrous methanol to form the corresponding naphthol, represented by graphic formula XIX (or more generally by XXV in Reaction G). Reaction E is further described in the text *Organic Reactions*, Vol. VI, Chapter 1, pages 1–73, John Wiley & Sons, Inc., New York.

REACTION D

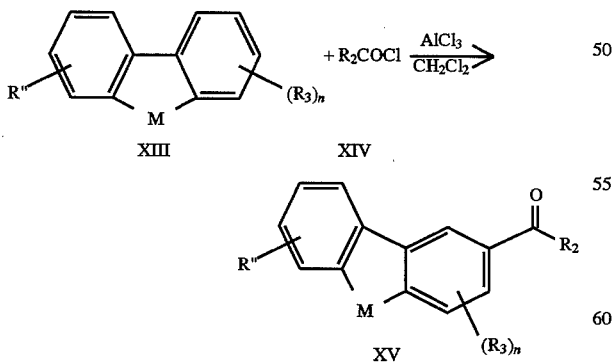

REACTION E

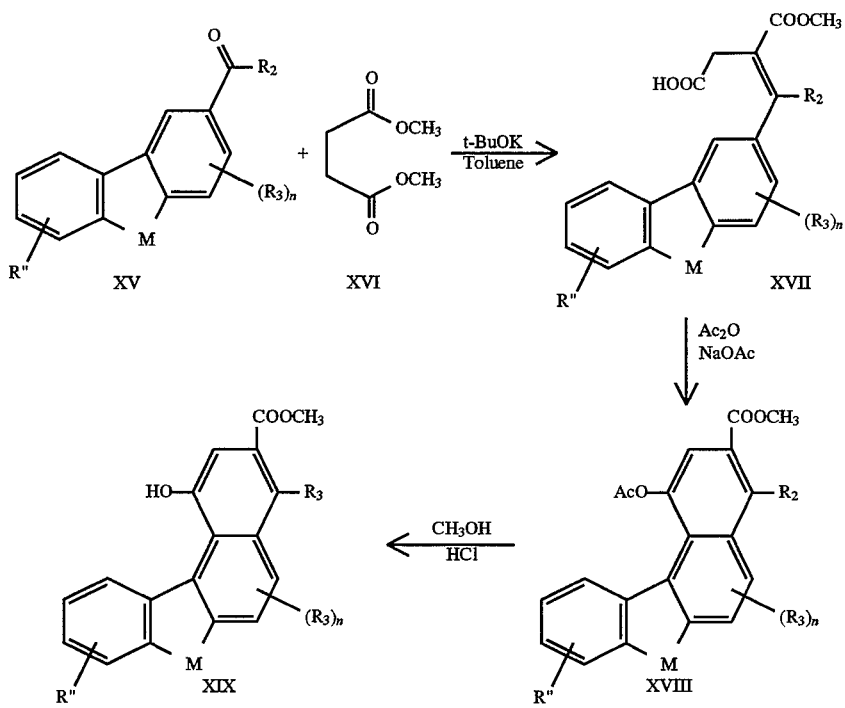

In Reaction F, when the A group is not present, a substituted or unsubstituted acetophenone, benzophenone, or benzaldehyde represented by graphic formula XX is reacted with dimethyl succinate (graphic formula XXI) in the presence of a base such as sodium hydride or potassium t-butoxide in a suitable solvent such as toluene or THF to form the appropriate substituted monoester of an α-arylidene succinic acid, represented by graphic formula XXII. Compound XXII is heated with acetic anhydride and anhydrous sodium acetate to form the corresponding acetate derivative represented by the graphic formula XXIII. Compound XXIII is reacted with hydrochloric acid and an anhydrous alcohol such as anhydrous methanol to form the corresponding naphthol, represented by graphic formula XXIV. Reaction F is further described in the text *Organic Reactions*, Vol. VI, Chapter 1, pages 1–73, John Wiley & Sons, Inc., New York.

REACTION F

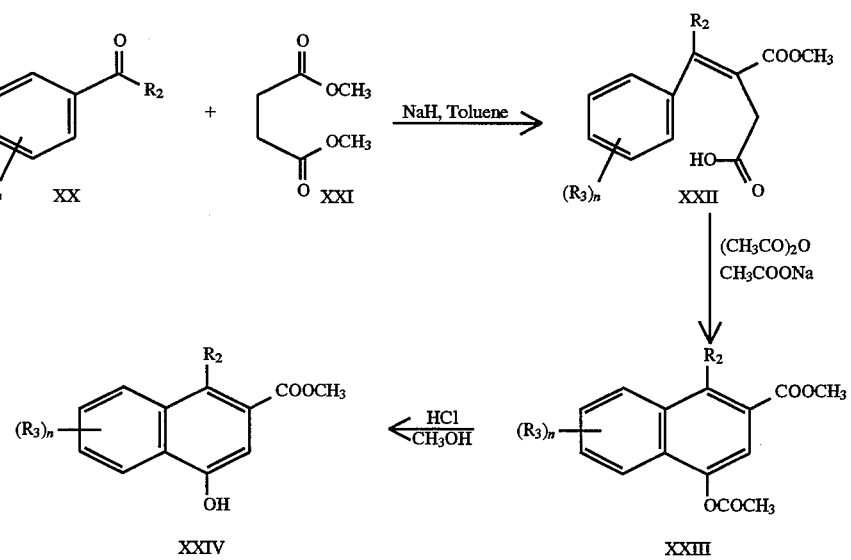

In Reaction G, the propargyl alcohol represented by graphic formula VI is coupled with the naphthol represented by graphic formula XXV A or the heteroaromatic fused naphthols represented by graphic formula XXV or XXV B to form compounds represented by graphic formula I (without side letters), I A (without atom numbers) or I B.

(b) 2-(4-methoxyphenyl)-2-(4-propoxyphenyl)-5-methoxycarbonyl-6-methyl-2H-benzofuro[2',3':7,8]naphtho[1,2-b]pyran;

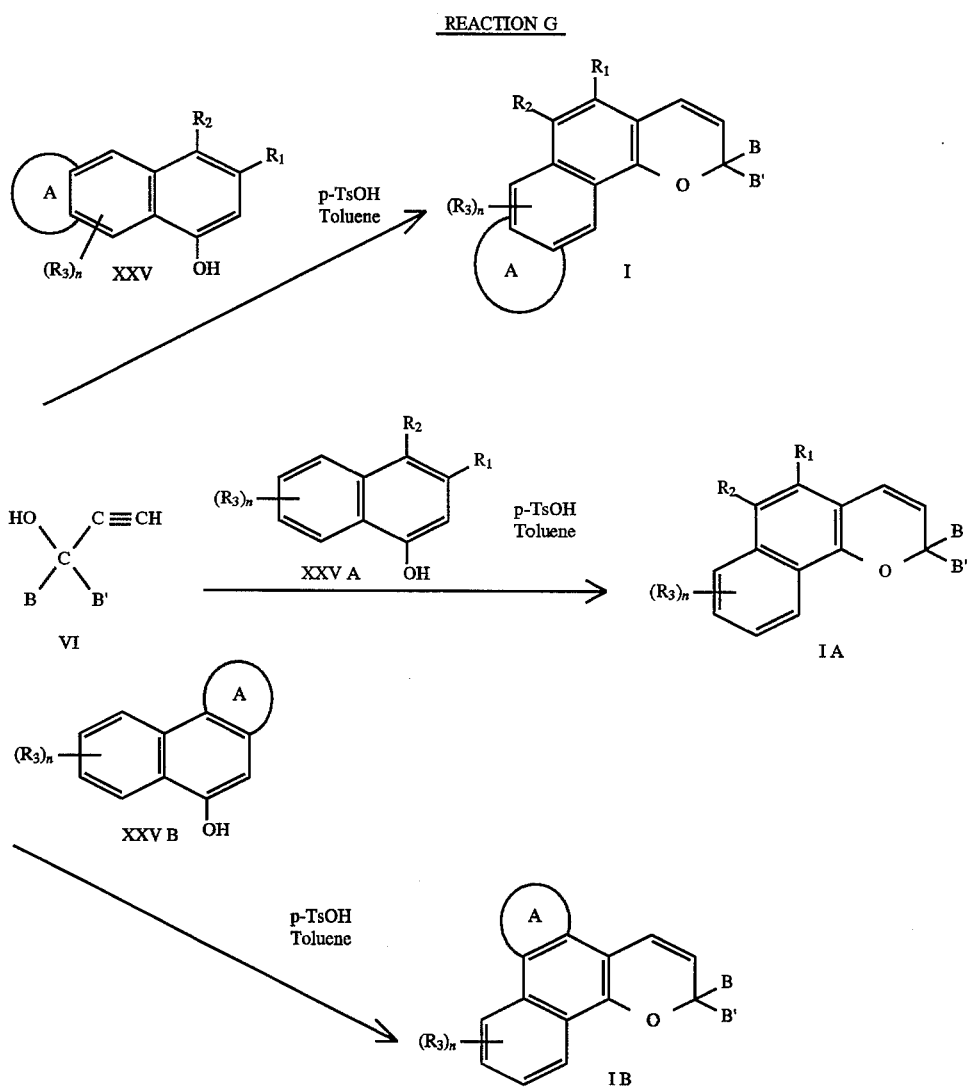

REACTION G

Compounds represented by graphic formulae I, I A and I B may be used in those applications in which organic photochromic substances may be employed, such as optical lenses, e.g., vision correcting ophthalmic lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. Naphthopyrans represented by graphic formulae I, I A and I B may exhibit color changes from colorless to colors ranging from yellow to blue.

Examples of contemplated naphthopyrans within the scope of the invention are the following:

(a) 2,2-bis(4-methoxyphenyl)-5-methoxycarbonyl-6-methyl-2H-benzofuro[2',3':7,8]naphtho[1,2-b]pyran;

(c) 2,2'-spiroadamantylene-5-methoxycarbonyl-6-methyl-2H-benzofuro[2',3':7,8]naphtho[1,2-b]pyran;

(d) 3,3-bis(4-methoxyphenyl)-10-methoxy-3H-naphtho[2",1":4',5']furo[2',3':3,4]naphtho[1,2-b]pyran;

(e) 3,3-bis(4-methoxyphenyl)-3H-naphtho[1",2":4',5']furo[3',2':3,4]naphtho[1,2-b]pyran;

(f) 3,3'-spiroadamantylene-3H-naphtho[1",2":4',5']furo[3',2':3,4]naphtho[1,2-b]pyran;

(g) 2,2-diphenyl-8-fluoro-5-methoxycarbonyl-2H-naphtho[1,2-b]pyran;

(h) 2,2-diphenyl-5-methoxycarbonyl-8-phenoxy-2H-naphtho[1,2-b]pyran; and (i) 2,2-bis(4-methoxyphenyl)-5-methoxycarbonyl-6-methyl-2H-indeno[3',2':7:8]naphtho[1,2-b]pyran.

It is contemplated that the organic photochromic naphthopyrans of the present invention may be used alone, in combination with other naphthopyrans of the present invention, or in combination with one or more other appropriate complementary organic photochromic materials, i.e., organic photochromic compounds having at least one activated absorption maxima within the range of between about 400 and 700 nanometers, or substances containing same, and may be incorporated, e.g., dissolved or dispersed, in a polymeric organic host material used to prepare photochromic articles and which color when activated to an appropriate hue.

Other than in the operating examples, or where otherwise indicated, all numbers expressing wavelengths, quantities of ingredients or reaction conditions used herein are to be understood as modified in all instances by the term "about".

Examples of complementary organic photochromic compounds include other naphthopyrans, benzopyrans, phenanthropyrans, spiro(benzindoline)naphthopyrans, spiro(indoline)benzopyrans, spiro(indoline)naphthopyrans, spiro(indoline)quinopyrans, spiro(indoline)pyrans, spiro(indoline)naphthoxazines, spiro(indoline)pyridobenzoxazines, spiro(benzindoline)pyridobenzoxazines, spiro(benzindoline)naphthoxazines, spiro(indoline)benzoxazines, and mixtures of such photochromic compounds.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, N.Y. (1981). As used herein, a near neutral color is one in which the chromaticity coordinate values of "x" and "y" for the color are within the following ranges (D65 illuminant): x=0.260 to 0.400, y=0.280 to 0.400 following activation to 40 percent luminous transmission by exposure to solar radiation (Air Mass 1 or 2).

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from about 0.05 to about 1.0, e.g., from 0.1 to about 0.45, milligrams per square centimeter of surface to which the photochromic substance(s) is incorporated or applied.

The photochromic substances of the present invention may be applied to or incorporated into a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; and applying the photochromic substance as part of a coating placed on the surface of the host material. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

The host material will usually be transparent, but may be translucent or even opaque. The host material need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

Examples of polymeric organic host materials which may be used with the photochromic substances or compositions described herein include: polymers, i.e., homopolymers and copolymers, of polyol(allyl carbonate) monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol methacrylate monomers and alkoxylated polyhydric alcohol acrylate monomers, such as ethoxylated trimethylol propane triacrylate monomers; polymers, i.e., homopolymers and copolymers, of polyfunctional, e.g., mono-, di- or multi-functional, acrylate and/or methacrylate monomers, poly($C_1$–$C_{12}$ alkyl methacrylates), such as poly(methyl methacrylate), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, polyesters, poly(ethylene terephthalate), polystyrene, poly(alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol methacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly, contemplated is use of the photochromic naphthopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66. Specifically contemplated are optical resins sold by PPG Industries, Inc. under the designation CR-307 and CR-407.

The present invention is more particularly described in the following examples which are intended as illustrative only, since numerous modifications and variations therein will be apparent to those skilled in the art.

EXAMPLE 1

Step 1

4,4'-Dimethoxybenzophenone (0.27 moles) was dissolved in a reaction flask containing 200 milliliters (ml) of anhydrous tetrahydrofuran saturated with acetylene and stirred at room temperature. An 18 weight percent suspension of sodium acetylide in xylene/mineral oil (0.3 mole of sodium acetylide) was added to the reaction flask and the mixture was stirred. After stirring 16 hours at room temperature under a nitrogen atmosphere, the contents of the reaction flask was added to a 5 weight percent aqueous hydrochloric acid and ice mixture. The resulting mixture was extracted with diethyl ether. The organic layer was separated, washed and dried over anhydrous sodium sulfate. The solvents, diethyl ether and tetrahydrofuran, were removed under vacuum to yield an oily product containing 1,1-bis(4-methoxyphenyl)-2-propyn-1-ol, which was crystallized from diethyl ether:hexane mixture. The recovered product (about 60 grams (g)) had a melting point of 83°–84° C. A nuclear magnetic resonance (NMR) showed the product to have a structure consistent with 1,1-bis(4-methoxyphenyl)-2-propyn-1-ol.

Step 2

2-Acetyldibenzofuran (50 g, 0.23 mole) and dimethyl succinate (40 g) were added to a flask containing 500 ml of toluene. Potasium t-butoxide (30 g) was slowly added to the reaction mixture and refluxed for three hours. Distilled water (400 ml) was added to the mixture and stirred for half hour. The aqueous layer was separated, washed with 50 ml of toluene and acidified with concentrated HCl. The resulting mixture was extracted with toluene and dried over anhydrous sodium sulfate. The solvent, toluene, was removed under vacuum to yield an oily product (about 55 g) containing 4-dibenzofur-2-yl-4-methyl-3-methoxycarbonyl-3-butenoic acid, which was not purified further but used directly in the next step.

Step 3

The product of Step 2 containing 4-dibenzofur-2-yl-4-methyl-3-methoxycarbonyl-3-butenoic acid and 40 g of anhydrous sodium acetate were added to a reaction flask containing 150 ml of acetic anhydride and refluxed for 4 hours. The mixture was cooled to room temperature and the solvent was removed under vacuum. Chloroform (300 ml) and water (300 ml) were added and the resulting mixture was stirred for two hours. The organic layer was separated, washed with distilled water and dried over anhydrous sodium sulfate. The solvent, chloroform, was removed under vacuum to yield an oily product containing 1-acetoxy-3-methoxycarbonyl-4-methyl-benzo(b)naphtho[1,2-d]furan, which was crystallized from diethyl ether. Approximately 38 g of the isolated product was recovered. A nuclear magnetic resonance (NMR) showed the product to have a structure consistent with 1-acetoxy-3-methoxycarbonyl-4-methyl-benzo(b)naphtho[1,2-d]furan.

Step 4

1-Acetoxy-3-methoxycarbonyl-4-methyl-benzo(b) naphtho[1,2-d]furan (35 g) from Step 3 and 1 ml of concentrated HCl were added to a reaction flask containing 150 ml of methanol and refluxed for five hours. The mixture was concentrated to 50 ml and the product crystallized at room temperature. Approximately 30 g of the isolated product was recovered. A nuclear magnetic resonance (NMR) showed the product to have a structure consistent with 1-hydroxy-3-methoxycarbonyl-4-methyl-benzo(b)naphtho[1,2-d]furan.

Step 5

1,1-Bis(4-methoxyphenyl)-2-propyn-1-ol (about 0.018 mole) from Step 1 and 1-hydroxy-3-methoxycarbonyl-4- methyl-benzo(b)naphtho[1,2-d]furan (5 g, 0.016 mole) from Step 4 were added to a reaction flask containing 75 ml of toluene and stirred. A catalytic amount of p-toluene-sulfonic acid (about 100 milligrams) was added, and the mixture was stirred for 4 hours. Afterwards, the reaction mixture was poured into a 10 weight percent sodium hydroxide solution. The organic layer was separated, washed with water, and dried over anhydrous sodium sulfate. The remaining solvent, toluene, was removed under vacuum. The resulting oil was purified using a silica gel column and a 1:3 mixture of chloroform:hexane as the eluant. The photochromic fractions were combined and the eluent was removed under vacuum. The resulting product was induced to crystallize from hexane. The recovered product (about 6 g) had a melting point of 207°–209° C. A nuclear magnetic resonance (NMR) spectrum showed the product to have a structure consistent with 2,2-bis(4-methoxyphenyl)-5-methoxycarbonyl-6-methyl-2H-benzofuro[2',3':7,8]naphtho[1,2-b]pyran.

EXAMPLE 2

The procedure of Example 1 was followed except that in Step 1, 4-methoxy-4'-propoxybenzophenone was used in place of 4,4'-dimethoxybenzophenone. The resulting product had a melting point of 135°–137° C. A nuclear magnetic resonance (NMR) spectrum showed the product to have a structure consistent with 2-(4-methoxyphenyl)-2-(4-propoxyphenyl)-5-methoxycarbonyl-6-methyl-2H-benzofuro[2',3':7,8]naphtho[1,2-b]pyran.

EXAMPLE 3

The procedure of Example 1 was followed except that in Step 1, adamantanone was used in place of 4,4'-dimethoxybenzophenone. The resulting product had a melting point of 174°–176° C. A nuclear magnetic resonance (NMR) spectrum showed the product to have a structure consistent with 2,2'-spiroadamantylene-5-methoxycarbonyl-6-methyl-2H-benzofuro[2',3':7,8]naphtho[1,2-b]pyran.

EXAMPLE 4

Step 1

1,4-Naphthoquinone (10 g, 0.062 mole) and 1,3-dihydroxynaphthalene (10 g, 0.062 mole) were added to a reaction flask containing 80 ml of acetic acid. Sulfuric acid (6.0 ml of 50 weight percent aqueous solution) was added to the reaction mixture and the mixture was refluxed for 2 hours. The reaction mixture was cooled to room temperature. The resulting precipitate that formed was collected by filtration, washed with cold acetic acid and dried. Approximately 13 g of the isolated product was recovered. A nuclear magnetic resonance (NMR) spectrum showed the product to have a structure consistent with 5,12-dihydroxydinaphtho[1,2-b:1',2'-d]furan.

Step 2

5,12-Dihydroxydinaphtho[1,2-b:1',2'-d]furan (5 g) from Step 1 and concentrated sulfuric acid (15 ml) were added to a reaction flask containing 30 ml of methanol and the mixture was refluxed for 5 hour. The reaction mixture was cooled to room temperature and poured into 300 ml of water. The resulting precipitate was collected by filtration, washed with water and dried. Approximately 4.5 g of the isolated product was recovered. A nuclear magnetic resonance (NMR) spectrum showed the product to have a structure consistent with 5-hydroxy-12-methoxydinaphtho[1,2-b:1',2'-d]furan.

Step 3

The procedure of Step 5 of Example 1 was followed except that 5-hydroxy-12-methoxydinaphtho[1,2-b:1',2'-d]furan from Step 2 was used in place of 1-hydroxy-3-methoxycarbonyl-4-methyl-benzo(b)naphtho[1,2-d]furan. The resulting product had a melting point of 198°–200° C. A nuclear magnetic resonance (NMR) spectrum showed the product to have a structure consistent with 3,3-Bis(4-methoxyphenyl)-10-methoxy-3H-naphtho[2",1":4',5']furo[2',3':3,4]naphtho[1,2-b]pyran.

EXAMPLE 5

Step 1

The procedure of Step 1 of Example 4 was followed except that 2-hydroxynaphthalene was used in place of 1,3-dihydroxynaphthalene to produce 12-hydroxydinaphtho[1,2-b:1',2'-d]furan.

Step 2

The procedure of Step 5 of Example 1 was followed except that 12-hydroxydinaphtho[1,2-b:1',2'-d]furan was used in place of 1-hydroxy-3-methoxycarbonyl-4-methyl-benzo(b)naphtho[1,2-d]furan. The resulting product had a melting point of 211°–213° C. A nuclear magnetic resonance (NMR) spectrum showed the product to have a structure consistent with 3,3-Bis(4-methoxyphenyl)-3H-naphtho[1", 2":4',5']furo[3',2':3,4]naphtho[1,2-b]pyran.

EXAMPLE 6

Step 1

The procedure of Step 1 of Example 1 was followed except that adamantanone was used in place of 4,4'-dimethoxybenzophenone to produce 2-ethinyl-2-hydroxyadamantane.

Step 2

The procedure of Step 5 of Example 1 was followed except that 12-hydroxydinaphtho[1,2-b:1',2'-d]furan from Step 1 of Example 5 was used in place of 1-hydroxy-3-methoxycarbonyl-4-methyl-benzo(b)naphtho[1,2-d]furan and 2-ethinyl-2-hydroxyadamantane from Step 1 was used in place of 1,1-bis(4-methoxyphenyl)-2-propyn-1-ol. The resulting product had a melting point of 125° C. A nuclear magnetic resonance (NMR) spectrum showed the product to have a structure consistent with 3,3'-spiroadamantylene-3H-naphtho[1",2":4',5']furo[3',2':3,4]naphtho[1,2-b]pyran.

EXAMPLE 7

The procedure of Example 1 was followed except for the following: Step 1 was omitted; in Step 2, 3-fluorobenzaldehyde was used in place of 2-acetyldibenzofuran; and in Step 5, 1,1-diphenyl-2-propyn-1-ol was used in place of 1,1-Bis(4-methoxyphenyl)-2-propyn-1-ol. Approximately 3.0 g of the isolated product was recovered. A nuclear magnetic resonance (NMR) spectrum showed the product to have a structure consistent with 2,2-diphenyl-8-fluoro-5-methoxycarbonyl-2H-naphtho[1,2-b]pyran.

EXAMPLE 8

The procedure of Example 7 was followed except that 3-phenoxybenzaldehyde was used in place of 3-fluorobenzaldehyde. Approximately 1.0 g of the isolated product was recovered. A nuclear magnetic resonance (NMR) spectrum showed the product to have a structure consistent with 2,2-diphenyl-5-methoxycarbonyl-8-phenoxy-2H-naphtho[1,2-b]pyran.

EXAMPLE 9

Step 1

The procedure of Example 1 was followed except that in Step 2, 2-acetylfluorene was used in place of 2-acetyldibenzofuran. Approximately 1.5 g of the isolated product was recovered. A nuclear magnetic resonance (NMR) spectrum showed the product to have a structure consistent with 2,2-bis(4-methoxyphenyl)-5-methoxycarbonyl-6-methyl-2H-indeno[3',2':7:8]naphtho[1,2-b]pyran.

EXAMPLE 10

Part A

Testing was done with the photochromic naphthopyrans of the Examples 1–8 incorporated into polymeric samples by the following method. The quantity of naphthopyran calculated to yield a 1.5 times $10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The naphthopyran was dissolved into the monomer blend by stirring and gentle heating, if necessary. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven set to increase the temperature from 40° C. to 95° C. over a 5 hour interval, hold the temperature at 95° C. for 3 hours and then lower it to 60° C. for at least 2 hours before the end of the curing cycle. After the mold was opened, the polymer sheet was cut using a diamond blade saw into 2 inch (5.1 centimeters) test squares.

The naphthopyran of Example 9 was imbibed by thermal transfer into a test square prepared from a diethylene glycol bis(allyl carbonate) composition sold by PPG Industries, Inc. under the designation CR-307 optical resin, by the following procedure. The naphthopyran was dissolved into a toluene solvent to form a 4 weight percent solution of the compound. A piece of No. 4 Whatman filter paper was saturated with the naphthopyran solution and allowed to air dry. The dried filter paper was placed on one side of the polymer test square, which measured ⅛ inch (0.3 centimeter)×2 inch (5.1 centimeters)×2 inch (5.1 centimeters). A piece of untreated filter paper was placed on the other side of the test square and the resulting sandwich placed between two plates of flat aluminum metal plates. The entire assembly was then placed in a 155° C. oven for a time sufficient to thermally transfer the naphthopyran into the test square. The imbibed test square was washed with acetone after removal from the oven.

Part B

The photochromic test squares prepared in Part A were tested for photochromic response rates on an optical bench. Prior to testing on the optical bench, the photochromic test squares were exposed to 365 nanometer ultraviolet light for about 15 minutes to activate the photochromic compounds and then placed into a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 75° F. (23.9° C.). The bench was fitted with a 150 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. A collimated beam of light from a tungsten lamp was passed through the square at a small angle normal to the square. After passing through the square, the light from the tungsten lamp was directed through a photopic filter attached to a detector. The photopic filter passes wavelengths such that the detector mimics the response of the human eye. The output signals from the detector(s) were processed by a radiometer.

Change in optical density (ΔOD) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula ΔOD=log (100/% Ta) where % Ta is the percent transmittance in the activated state and the logarithm is to the base 10.

The ΔOD/Min, which represents the sensitivity of the photochromic compound's response to UV light, was measured over the first five (5) seconds of UV exposure, then expressed on a per minute basis. The saturation optical density (OD) was taken under identical conditions as the ΔOD/Min, except UV exposure was continued for 20 minutes for the examples in Table 1. The lambda max reported in Table 1 is the wavelength in the visible spectrum at which the maximum absorption of the activated (colored) form of the photochromic compound in the test square occurs. The Bleach Rate (T ½) is the time interval in seconds for the absorbance of the activated form of the naphthopyran in the test squares to reach one half the highest absorbance at room temperature (75° F., 23.9° C.) after removal of the source of activating light. Results for the Compounds of the Examples are tabulated in Table 1.

TABLE 1

| EXAMPLE COMPOUNDS | LAMBDA MAX (VISIBLE) | ΔOD/MIN SENSITIVITY | ΔOD@ SATURATION | Bleach (T1/2) |
| --- | --- | --- | --- | --- |
| 1 | 538 nm | 0.21 | 0.28 | 55 |
| 2 | 533 nm | 0.20 | 0.22 | 57 |
| 3 | 472 nm | 0.20 | 0.14 | 126 |
| 4 | 583 nm | 0.24 | 0.44 | 125 |
| 5 | 512 nm | 0.15 | 0.11 | 34 |
| 6 | 473 nm | 0.11 | 0.05 | 319 |
| 7 | 463 nm | 0.23 | 0.20 | 36 |
| 8 | 463 nm | 0.42 | 0.43 | 80 |
| 9 | 529 nm | 0.36 | 0.59 | 677 |

The results of Table 1 show that a range of values for bleach rate, ΔOD at saturation, and sensitivity are obtained for the Example Compounds 1 through 9 of the present invention depending on the nature of the heterocyclic ring A, the side of fusion, and the substituents $R_1$, $R_2$, $R_3$, B and B'.

Although the present invention has been described with reference to the specific details of particular embodiments thereof, it is not intended that such details be regarded as limitations upon the scope of the invention except as and to the extent that they are included in the accompanying claims.

We claim:

1. A naphthopyran compound represented by the following graphic formulae:

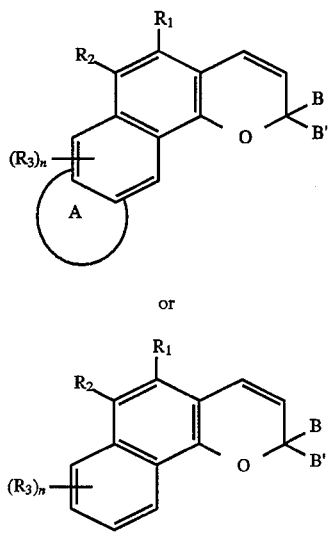

or wherein, (a) A is selected from the group consisting of:
 (i) an unsubstituted, mono-substituted or di-substituted heterocyclic ring selected from the group consisting of benzothieno, benzofurano and indolo, the 2,3 or 3,2 positions of said heterocyclic ring being fused to the i, j or k side of said naphthopyran; and
 (ii) an unsubstituted, mono-substituted or di-substituted indeno group fused to the i, j or k side of said naphthopyran; each of said heterocyclic ring and indeno group substituents being $C_1$–$C_6$ alkyl, $C_5$–$C_7$ cycloalkyl, $C_1$–$C_6$ alkoxy, chloro, fluoro, a benzo or mono-substituted benzo group fused to the benzo portion of the benzothieno, benzofurano, indeno or indolo moiety, said benzo substitutent being $C_1$–$C_6$ alkyl, $C_5$–$C_7$ cycloalkyl, $C_1$–$C_6$ alkyl mono-substituted ($C_5$–$C_7$)cycloalkyl, $C_1$–$C_6$ alkoxy, chloro or fluoro;

(b) $R_1$ is selected from the group consisting of:
 (i) —C(O)W, W being —$OR_4$ or —$N(R_5)R_6$, wherein $R_4$ is hydrogen, allyl, $C_1$–$C_6$ alkyl, phenyl, mono-substituted phenyl, phenyl($C_1$–$C_3$)alkyl, mono-substituted phenyl($C_1$–$C_3$)alkyl, mono($C_1$–$C_6$) alkoxy($C_2$–$C_4$)alkyl, $C_1$–$C_6$ chloroalkyl or $C_1$–$C_6$ fluoroalkyl; $R_5$ and $R_6$ are each selected from the group consisting of hydrogen, $C_1$–$C_6$ alkyl, $C_5$–$C_7$ cycloalkyl, unsubstituted, mono-substituted and di-substituted phenyl, or $R_5$ and $R_6$ together with the nitrogen atom form an unsubstituted, mono-substituted or di-substituted heterocyclic ring selected from the group consisting of 1-indolinyl, morpholino, piperidino, 1-pyrrolidyl, 1-imidazolidyl, 2-imidazolin-1-yl, pyrazolidyl, pyrazolinyl and 1-piperazinyl; and
 (ii) —$C(R_{11})_2X$, wherein X is —CN, chloro, fluoro, hydroxy, benzoyloxy, $C_1$–$C_6$ alkoxy, $C_2$–$C_6$ acyloxy, amino, $C_1$–$C_6$ mono-alkylamino, $C_1$–$C_6$ dialkylamino, morpholino, piperidino, 1-indolinyl, pyrrolidyl, or trimethylsilyloxy, $R_{11}$ is hydrogen, $C_1$–$C_6$ alkyl, phenyl or naphthyl, and each of said phenyl and heterocyclic ring substituents in this part (b) being $C_1$–$C_6$ alkyl or $C_1$–$C_6$ alkoxy;

(c) $R_2$ is hydrogen, $C_1$–$C_6$ alkyl, the mono-, di- or tri-substituted aryl groups phenyl or naphthyl, said aryl substituents being $C_1$–$C_6$ alkyl, $C_1$–$C_6$ alkoxy, chloro or fluoro; or (d) $R_1$ and $R_2$ together form the heterocyclic ring A, as defined in part(a)(i), provided that the 2,3 or 3,2 positions of said heterocyclic ring are fused to the f side of said naphthopyran, and provided further there is only one heterocyclic ring A fused to the naphthopyran;

(e) each $R_3$ is chloro, fluoro, $C_1$–$C_6$ alkyl, $C_1$–$C_6$ alkoxy, phenyl, naphthyl, phenoxy, naphthoxy or the group, —$N(R_5)R_6$, as defined in (b)(i), and n is selected from the integers 0, 1 or 2, provided that group A, as defined in (a), is present, or each $R_3$ is chloro, fluoro, phenoxy, naphthoxy or the group, —$N(R_5)R_6$, and n is selected from the integers 1, 2 or 3, provided that group A is absent; and (f) B and B' are each selected from the group consisting of:
 (i) the unsubstituted, mono-, di- and tri-substituted aryl groups phenyl and naphthyl;
 (ii) the unsubstituted, mono- and di-substituted heterocyclic aromatic groups pyridyl, furanyl, benzofuran-2-yl, benzofuran-3-yl, thienyl, benzothien-2-yl, benzothien-3-yl, dibenzothienyl, dibenzofuranyl, and carbazolyl, said aryl and heterocyclic substituents described in (i) and (ii) being selected from the group consisting of hydroxy, amino, $C_1$–$C_6$ monoalkylamino, $C_1$–$C_6$ dialkylamino, morpholino, piperidino, 1-indolinyl, pyrrolidyl, 1-imidazolidyl, 2-imidazolin-1-yl, 2-pyrazolidyl, pyrazolinyl, 1-piperazinyl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$) alkoxy($C_1$–$C_4$)alkyl, acryloxy, methacryloxy, fluoro and chloro;
 (iii) the groups represented by the following graphic formulae:

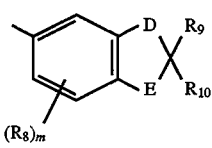 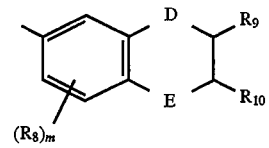

wherein D is carbon or oxygen and E is oxygen or substituted nitrogen, provided that when E is substituted nitrogen, D is carbon, said nitrogen substituent being selected from the group consisting of hydrogen, $C_1$–$C_6$ alkyl, and $C_2$–$C_6$ acyl; each $R_8$ is $C_1$–$C_6$ alkyl, $C_1$–$C_6$ alkoxy, hydroxy, chloro or fluoro; $R_9$ and $R_{10}$ are each hydrogen or $C_1$–$C_6$ alkyl; and m is the integer 0, 1 or 2;
 (iv) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$)alkoxy($C_3$–$C_6$) cycloalkyl, mono($C_1$–$C_6$)alkyl($C_3$–$C_6$) cycloalkyl, chloro ($C_3$–$C_6$)cycloalkyl and fluoro($C_3$–$C_6$)cycloalkyl; and
 (v) the group represented by the following graphic formula:

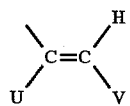

wherein U is hydrogen or $C_1$-$C_4$ alkyl, and V is selected from the unsubstituted, mono- and di-substituted members of the group consisting of naphthyl, phenyl, furanyl and thienyl, wherein the substituents for each member of said group are $C_1$-$C_4$ alkyl, $C_1$-$C_4$ alkoxy, fluoro or chloro; or (vi) B and B' taken together form fluoren-9-ylidene, mono- or di-substituted fluoren-9-ylidene or a member selected from the group consisting of saturated $C_3$-$C_{12}$ spiro-monocyclic hydrocarbon rings, saturated $C_7$-$C_{12}$ spiro-bicyclic hydrocarbon rings, and saturated $C_7$-$C_{12}$ spiro-tricyclic hydrocarbon rings, said fluoren-9-ylidene substituents being selected from the group consisting of $C_1$-$C_4$ alkyl, $C_1$-$C_4$ alkoxy, fluoro and chloro.

2. The naphthopyran of claim 1 wherein:
(a) A is selected from the group consisting of:
  (i) an unsubstituted or mono-substituted heterocyclic ring; and
  (ii) an unsubstituted or mono-substituted indeno group, each of said heterocyclic ring and indeno group substituents being $C_1$-$C_4$ alkyl, $C_1$-$C_3$ alkoxy or benzo;
(b) $R_1$ is selected from the group consisting of:
  (i) —C(O)W, W being —$OR_4$ or —$N(R_5)R_6$, wherein $R_4$ is hydrogen, $C_1$-$C_4$ alkyl, unsubstituted or mono-substituted phenyl, unsubstituted or mono-substituted phenyl($C_1$-$C_3$)alkyl, mono($C_1$-$C_4$) alkoxy($C_2$-$C_3$)alkyl, or $C_1$-$C_4$ haloalkyl, and wherein $R_5$ and $R_6$ are each selected from the group consisting of hydrogen, $C_1$-$C_4$ alkyl, $C_5$-$C_7$ cycloalkyl, unsubstituted, mono-substituted and di-substituted phenyl, or $R_5$ and $R_6$ together with the nitrogen atom form an unsubstituted, mono-substituted or di-substituted heterocyclic ring selected from the group consisting of 1-indolinyl, morpholino, piperidino, and 1-pyrrolidyl, each of said phenyl and heterocyclic ring substituents being $C_1$-$C_4$ alkyl or $C_1$-$C_4$ alkoxy; and
  (ii) —$C(R_{11})_2$X, wherein X is —CN, halogen, hydroxy, benzoyloxy, $C_1$-$C_4$ alkoxy, $C_2$-$C_4$ acyloxy, amino, $C_1$-$C_4$ mono-alkylamino, $C_1$-$C_4$ dialkylamino, morpholino, piperidino, 1-indolinyl or pyrrolidyl, and $R_{11}$ is hydrogen, $C_1$-$C_4$ alkyl, phenyl or naphthyl;
(c) $R_2$ is hydrogen, $C_1$-$C_4$ alkyl, the mono- or di-substituted aryl groups phenyl or naphthyl, said aryl substituents being $C_1$-$C_4$ alkyl or $C_1$-$C_4$ alkoxy, chloro or fluoro; or
(d) $R_1$ and $R_2$ together form the heterocyclic ring A, as defined in part (a);
(e) each $R_3$ is fluoro, $C_1$-$C_4$ alkyl, $C_1$-$C_4$ alkoxy, phenyl, naphthyl, phenoxy, naphthoxy, or the group, —$N(R_5)R_6$, as defined in (b)(i), and n is selected from the integers 0, 1 or 2, provided that group A, as defined in (a), is present, or each $R_3$ is fluoro, phenoxy, naphthoxy or the group, —$N(R_5)R_6$, and n is selected from the integers 1, 2 or 3, provided that group A is absent; and
(f) B and B' are each selected from the group consisting of:

(i) unsubstituted, mono-, di- and tri-substituted phenyl;
(ii) the unsubstituted, mono- and di-substituted heterocyclic aromatic groups pyridyl, furanyl, benzofuran-2-yl, benzofuran-3-yl, thienyl, benzothien-2-yl, benzothien-3-yl, dibenzothienyl, dibenzofuranyl, and carbazolyl, each of said aryl and heterocyclic substituents in this part (i) and (ii) being selected from the group consisting of morpholino, piperidino, $C_1$-$C_4$ alkyl, $C_1$-$C_4$ alkoxy and halogen, said halogen being fluoro or chloro;
(iii) the groups represented by the following graphic formula:

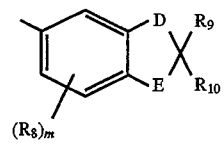

wherein D is carbon and E is oxygen; each $R_8$ is $C_1$-$C_4$ alkyl, $C_1$-$C_4$ alkoxy, hydroxy, or halogen, said halogen being chloro or fluoro; $R_9$ and $R_{10}$ are each hydrogen or $C_1$-$C_4$ alkyl; and m is the integer 0, 1 or 2;
(iv) $C_1$-$C_4$ alkyl, $C_1$-$C_6$ alkoxy($C_1$-$C_4$)alkyl, and $C_3$-$C_6$ cycloalkyl; and
(v) the group represented by the following graphic formula:

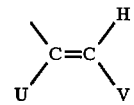

wherein U is hydrogen or methyl, and V is phenyl or mono-substituted phenyl, said phenyl substituent being $C_1$-$C_4$ alkyl, $C_1$-$C_4$ alkoxy or fluoro; or
(vi) B and B' taken together form an unsubstituted or mono-substituted fluoren-9-ylidene or a member selected from the group consisting of saturated $C_3$-$C_8$ spiro-monocyclic hydrocarbon rings, saturated $C_7$-$C_{10}$ spiro-bicyclic hydrocarbon rings, and saturated $C_7$-$C_{10}$ spiro-tricyclic hydrocarbon rings, said fluoren-9-ylidene substituents being selected from $C_1$-$C_3$ alkyl, $C_1$-$C_3$ alkoxy and fluoro.

3. The naphthopyran of claim 2 wherein:
(a) A is selected from the group consisting of:
  (i) an unsubstituted or mono-substituted heterocyclic ring, the 2,3 or 3,2 position of said heterocyclic ring being fused to the i or k side of said naphthopyran; and
  (ii) an unsubstituted or mono-substituted indeno group fused to the i or k side of said naphthopyran, said heterocyclic ring and indeno group substituents being $C_1$-$C_3$ alkyl, $C_1$-$C_3$ alkoxy or benzo;
(b) $R_1$ is selected from the group consisting of:
  (i) —C(O)W, W being —$OR_4$ or —$N(R_5)R_6$, wherein $R_4$ is hydrogen, $C_1$-$C_3$ alkyl, unsubstituted or mono-substituted phenyl, mono($C_1$-$C_3$)alkoxy($C_2$-$C_3$) alkyl, or $C_1$-$C_3$ fluoroalkyl, and wherein $R_5$ and $R_6$ are each selected from the group consisting of hydrogen, $C_1$-$C_3$ alkyl, $C_5$-$C_7$ cycloalkyl, unsubstituted and mono-substituted phenyl, or $R_5$ and $R_6$ together with the nitrogen atom form an unsubstituted or mono-substituted heterocyclic ring selected from the group consisting of morpholino and piperidino, each of said phenyl and heterocyclic ring substituents being $C_1$-$C_3$ alkyl or $C_1$-$C_3$ alkoxy; and (ii) —C(R₁₁)₂X, wherein X is fluoro, hydroxy, benzoyloxy, $C_1$–$C_3$ alkoxy, $C_2$–$C_3$ acyloxy, amino, $C_1$–$C_3$ monoalkylamino, $C_1$–$C_3$ dialkylamino, morpholino or piperidino, and $R_{11}$ is hydrogen, $C_1$–$C_3$ alkyl, phenyl or naphthyl;

(c) $R_2$ is hydrogen, $C_1$–$C_3$ alkyl, the mono- or di-substituted aryl groups, phenyl or naphthyl, said aryl substituents being $C_1$–$C_3$ alkyl, $C_1$–$C_3$ alkoxy or fluoro; or (d) $R_1$ and $R_2$ together form the heterocyclic ring A, as defined in part (a);

(e) each $R_3$ is fluoro, $C_1$–$C_3$ alkyl, $C_1$–$C_3$ alkoxy, phenoxy, naphthoxy, or the group, —N(R₅)R₆, as defined in (b)(i), and n is selected from the integers 0 or 1, provided that group A, as defined in (a), is present, or each $R_3$ is fluoro, phenoxy, naphthoxy, or the group, —N(R₅)R₆, and n is selected from the integers 1 or 2, provided that group A is absent; and (f) B and B' are each selected from the group consisting of:
 (i) unsubstituted, mono-, and di-substituted phenyl;
 (ii) the unsubstituted, mono- and di-substituted heterocyclic aromatic groups pyridyl, benzofuran-2-yl, benzothien-2-yl, dibenzothienyl and dibenzofuranyl, each of said phenyl and heterocyclic substituents in parts (i) and (ii) being selected from the group consisting of morpholino, piperidino, $C_1$–$C_2$ alkyl and $C_1$–$C_2$ alkoxy; and
 (iii) the groups represented by the following graphic formula:

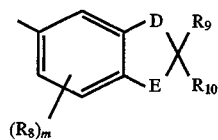

wherein D is carbon and E is oxygen; each $R_8$ is $C_1$–$C_2$ alkyl, $C_1$–$C_2$ alkoxy or fluoro; $R_9$ and $R_{10}$ are each hydrogen or $C_1$–$C_2$ alkyl; and m is the integer 0, 1 or 2; or (iv) B and B' taken together form fluoren-9-ylidene, bornylidene, norbornylidene, bicyclo[3.3.1]nonan-9-ylidene or adamantylidene.

4. The naphthopyran of claim 3 wherein:

(a) A is selected from the group consisting of an unsubstituted or mono-substituted benzothieno, benzofurano or indeno group, each of said group substituents being $C_1$–$C_2$ alkyl, $C_1$–$C_2$ alkoxy or benzo;

(b) $R_1$ is selected from the group consisting of:
 (i) —C(O)W, W being —OR₄ or —N(R₅)R₆, wherein $R_4$ is $C_1$–$C_3$ alkyl, $R_5$ and $R_6$ are each hydrogen, $C_1$–$C_3$ alkyl or phenyl, or $R_5$ and $R_6$ together with the nitrogen atom form morpholino or piperidino; and
 (ii) —C(R₁₁)₂X, wherein X is fluoro, hydroxy, $C_1$–$C_2$ alkoxy, acetoxy, amino, $C_1$–$C_2$ mono-alkylamino, $C_1$–$C_2$ dialkylamino, morpholino or piperidino, and $R_{11}$ is hydrogen or $C_1$–$C_2$ alkyl;

(c) $R_2$ is hydrogen, $C_1$–$C_2$ alkyl, mono- or di-substituted phenyl, said phenyl substituents being $C_1$–$C_2$ alkyl or $C_1$–$C_2$ alkoxy or fluoro; or (d) $R_1$ and $R_2$ together form an unsubstituted or monosubstituted benzothieno or benzofurano group;

(e) each $R_3$ is fluoro, $C_1$–$C_2$ alkyl, $C_1$–$C_2$ alkoxy, phenoxy, naphthoxy, or the group, —N(R₅)R₆, as defined in (b)(i), and n is selected from the integers 0 or 1, provided that group A, as defined in (a), is present, or each $R_3$ is fluoro, phenoxy, naphthoxy, or the group, —N(R₅)R₆, and n is selected from the integers 1 or 2, provided that group A is absent; and (f) B and B' are each phenyl, methoxy substituted phenyl, morpholino substituted phenyl, dibenzofuran-2-yl 2,3-dihydrobenzofuran-5-yl or adamantylidene.

5. A naphthopyran compound selected from the group consisting of:

(a) 2,2-bis(4-methoxyphenyl)-5-methoxycarbonyl-6-methyl-2H-benzofuro[2',3':7,8]naphtho[1,2-b]pyran;

(b) 2-(4-methoxyphenyl)-2-(4-propoxyphenyl)-5-methoxycarbonyl-6-methyl-2H-benzofuro[2',3':7,8]naphtho[1,2-b]pyran;

(c) 2,2'-Spiroadamantylene-5-methoxycarbonyl-6-methyl-2H-benzofuro[2',3':7,8]naphtho[1,2-b]pyran;

(d) 3,3-Bis(4-methoxyphenyl)-10-methoxy-3H-naphtho[2",1":4',5']furo[2',3':3,4]naphtho[1,2-b]pyran;

(e) 3,3-Bis(4-methoxyphenyl)-3H-naphtho[1",2":4',5']furo[3',2':3,4]naphtho[1,2-b]pyran;

(f) 3,3'-Spiroadamantylene-3H-naphtho[1",2":4',5']furo[3',2':3,4]naphtho[1,2-b]pyran;

(g) 2,2-diphenyl-8-fluoro-5-methoxycarbonyl-2H-naphtho[1,2-b]pyran;

(h) 2,2-diphenyl-5-methoxycarbonyl-8-phenoxy-2H-naphtho[1,2-b]pyran; and (i) 2,2-bis(4-methoxyphenyl)-5-methoxycarbonyl-6-methyl-2H-indeno[3',2':7:8]naphtho[1,2-b]pyran.

6. A photochromic article comprising a polymeric organic host material and a photochromic amount of a naphthopyran compound of claim 1.

7. The photochromic article of claim 6 wherein the polymeric organic host material is selected from the group consisting of polyacrylates, polymethacrylates, poly($C_1$–$C_{12}$ alkyl methacrylates), polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

8. A photochromic article comprising a polymeric organic host material and a photochromic amount of a naphthopyran compound of claim 2.

9. The photochromic article of claim 8 wherein the polymeric organic host material is selected from the group consisting of polyacrylates, polymethacrylates, poly($C_1$–$C_{12}$ alkyl methacrylates), polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

10. The photochromic article of claim 9 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, diisopropenyl benzene monomers, and ethoxylated trimethylol propane triacrylate monomers.

11. The photochromic article of claim 10 wherein the photochromic compound is present in an amount of from about 0.05 to 1.0 milligram per square centimeter of organic host material surface to which the photochromic substance (s) is incorporated or applied.

12. The photochromic article of claim 11 wherein the article is a lens.

13. A photochromic article comprising a photochromic amount of the naphthopyran compound of claim 3 and a polymeric organic host material selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, diisopropenyl benzene monomers, and ethoxylated trimethylol propane triacrylate monomers.

14. A photochromic article comprising a photochromic amount of the naphthopyran compound of claim 4 and a polymeric organic host material selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, diisopropenyl benzene monomers, and ethoxylated trimethylol propane triacrylate monomers.

15. A photochromic article comprising, in combination, a solid transparent polymeric organic host material, and a photochromic amount of each of (a) at least one naphthopyran compound of claim 1, and (b) at least one other organic photochromic compound having at least one activated absorption maxima within the range of between about 400 and 700 nanometers.

16. The photochromic article of claim 15 wherein the polymeric organic host material is selected from the group consisting of polyacrylates, polymethacrylates, poly($C_1$–$C_{12}$ alkyl methacrylates), polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

17. The photochromic article of claim 16 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol methacrylate monomers, diisopropenyl benzene monomers and ethoxylated trimethylol propane triacrylate monomers.

18. The photochromic article of claim 15 wherein the organic photochromic compound (b) is selected from the group consisting of naphthopyrans, benzopyrans, phenanthropyrans, spiro(benzindoline)naphthopyrans, spiro (indoline)benzopyrans, spiro(indoline)naphthopyrans, spiro (indoline)quinopyrans, spiro(indoline)pyrans, spiro (indoline)naphthoxazines, spiro(indoline) pyridobenzoxazines, spiro(benzindoline) pyridobenzoxazines, spiro(benzindoline)naphthoxazines, spiro(indoline)benzoxazines and mixtures of such photochromic compounds.

19. The photochromic article of claim 18 wherein the photochromic compound is present in an amount of from about 0.05 to 1.0 milligram per square centimeter of organic host material surface to which the photochromic substance (s) is incorporated or applied.

20. The photochromic article of claim 19 wherein the article is a lens.

21. A photochromic article comprising, in combination, a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol methacrylate monomers, diisopropenyl benzene monomers and ethoxylated trimethylol propane triacrylate monomers, and a photochromic amount of each of (a) at least one naphthopyran compound of claim 4, and (b) at least one other organic photochromic compound having at least one activated absorption maxima within the range of between about 400 and 700 nanometers.

\* \* \* \* \*